United States Patent [19]

Yamane et al.

[11] Patent Number: 4,663,294
[45] Date of Patent: May 5, 1987

[54] DNA CODING FOR A SIGNAL AMINO ACID SEQUENCE AND DNA CONTAINING THE SAME

[75] Inventors: Kunio Yamane, 614-201, Takezono 3-chome, Sakura-mura, Niihari-gun, Ibaragi-ken; Kazutaka Ohmura, Chiba; Akira Nakayama, Ibaragi; Yasutoshi Takeichi, Tokyo, all of Japan

[73] Assignees: Kunio Yamane, Ibaragi; The Calpis Food Industry Co., Ltd.; Mitsui Toatsu Chemicals, Inc., both of Tokyo, all of Japan

[21] Appl. No.: 568,629

[22] Filed: Jan. 6, 1984

[30] Foreign Application Priority Data

Jan. 25, 1983 [JP] Japan ............................. 58-010088

[51] Int. Cl.[4] .................... C12N 1/00; C12N 15/00; C07H 17/00
[52] U.S. Cl. ........................... 435/317; 435/172.3; 536/27; 935/24; 935/48
[58] Field of Search ............... 435/317, 172.3, 320; 935/14, 29, 48; 536/27

[56] References Cited

PUBLICATIONS

Debabou, V. G. in *The Molecular Biology of the Bacilli,* vol. I. (Dubnau, Ed.) Academic Press, p. 331–344 (1982).

Nagata, Y. *J. Bacteriology,* vol. 119, No. 2, pp. 425–430 (1974).

*Primary Examiner*—Thomas G. Wiseman
*Assistant Examiner*—Jayme A. Huleatt

[57] ABSTRACT

This invention relates to DNA consisting of a DNA base sequence coding for the signal amino acid sequence:

| Met | Phe | Ala | Lys | Arg | Phe | Lys |
|-----|-----|-----|-----|-----|-----|-----|
| Thr | Ser | Leu | Leu | Pro | Leu | Phe |
| Ala | Gly | Phe | Leu | Leu | Leu | Phe |
| Tyr | Leu | Val | Leu | Ala | Gly | Pro |
| Ala | Ala | Ala | Ser | Ala | Glu | Thr |
| Ala | Asn | Lys | Ser | Asn | Glu,   |    | and to DNA containing such a DNA base sequence. The DNA base sequence coding for said amino acid sequence includes, for example,

| ATG | TTT | GCA | AAA | CGA | TTC | AAA |
|-----|-----|-----|-----|-----|-----|-----|
| ACC | TCT | TTA | CTG | CCG | TTA | TTC |
| GCT | GGA | TTT | TTA | TTG | CTG | TTT |
| TAT | TTG | GTT | CTG | GCA | GGA | CCG |
| GCG | GCT | GCG | AGT | GCT | GAA | ACG |
| GCG | AAC | AAA | TCG | AAT | GAG. |    |

The desired products in cells can be secreted out of cells by the use of a vector containing DNA consisting of the DNA base sequence coding for said signal amino acid sequence.

5 Claims, No Drawings

DNA CODING FOR A SIGNAL AMINO ACID SEQUENCE AND DNA CONTAINING THE SAME

BACKGROUND OF THE INVENTION

This invention relates to DNA coding for a signal amino acid sequence which acts to secrete products out of cells and to DNA containing such a sequence.

The signal amino acid sequence herein means an amino acid sequence acting so that products which have been formed in cells can be secreted out of the cells. Generally, products are produced in cells and accumulated therein. On the other hand, those products which have a signal amino acid sequence are said to be secreted out of cells along with their formation therein. Accordingly, products in cells can successfully be secreted out of the cells if such a signal amino acid sequence is utilized.

Secretion of products out of cells could have the following merits: Firstly, if products in cells can be moved out of the cells, it will become possible to separate impurities from the products easily and to reduce the labor required for their purification and isolation procedures. In addition, the products in cells can be isolated in a pure state without being accompanied by poisonous substances contained in the cell membrane, so that they will have uses in a wide range, with no restriction in their application. Secondly, even when products in cells are such that their production in cells would be inhibited by their own excessive formation, they will be freed from the feedback inhibition as they are transferred out of the biosynthetic system, so that their excessive production will become possible. Thirdly, those products in cells which are harmful to the growth of cells can be moved out of the cells, so that their production can be carried on while the cells are maintained wholesome.

Several kinds of such signal amino acid sequences and DNA base sequences thereof have been known. They are, for example, a signal amino acid sequence for penicillinase for *Bacillus licheniformis* (Nucleic Acid Research Vol. 9, No. 11, 2577 (1981)) and a signal amino acid sequence for α-amylase for *Bacillus amyloliquefaciense* (Gene, 15, 43 (1981)).

The present inventors have carried out the cloning of α-amylase gene of *Bacillus subtilis* known for its very high α-amylase productivity, analyzed such cloned gene, and discovered a new signal amino acid sequence different from the known signal amino acid sequence and DNA base sequence thereof for amylase. As a result, they have invented a new signal amino acid sequence and DNA base sequence different from those heretofore known.

When production in cells is carried out using the DNA of this invention in a host vector system where the host is *Bacillus subtilis* which has a high α-amylase productivity, the system in this invention will be superior in stability and secretory productivity to the system used a different organism or a different signal amino acid sequence.

SUMMARY OF THE INVENTION

An object of this invention is to provide a new DNA base sequence coding for a new signal amino acid sequence consisting of

| Met | Phe | Ala | Lys | Arg | Phe | Lys |
|-----|-----|-----|-----|-----|-----|-----|
| Thr | Ser | Leu | Leu | Pro | Leu | Phe |
| Ala | Gly | Phe | Leu | Leu | Leu | Phe |
| Tyr | Leu | Val | Leu | Ala | Gly | Pro |
| Ala | Ala | Ala | Ser | Ala | Glu | Thr |
| Ala | Asn | Lys | Ser | Asn | Glu. |  | said DNA base sequence being preferably as follows:

| ATG | TTT | GCA | AAA | CGA | TTC | AAA |
|-----|-----|-----|-----|-----|-----|-----|
| ACC | TCT | TTA | CTG | CCG | TTA | TTC |
| GCT | GGA | TTT | TTA | TTG | CTG | TTT |
| TAT | TTG | GTT | CTG | GCA | GGA | CCG |
| GCG | GCT | GCG | AGT | GCT | GAA | ACG |
| GCG | AAC | AAA | TCG | AAT | GAG. |  |

DETAILED DESCRIPTION OF THE PREFERRED EMBODIMENTS

The chemical symbols used in this specification stand for the following compounds:

| Met | methionine |
|-----|------------|
| Phe | phenylalanine |
| Ala | alanine |
| Lys | lysine |
| Arg | arginine |
| Thr | threonine |
| Ser | serine |
| Leu | leucine |
| Pro | proline |
| Gly | glycine |
| Tyr | tyrosine |
| Val | valine |
| Glu | glutamic acid |
| Asn | asparagine |
| A | adenine |
| T | thymine |
| G | guanine |
| C | cytosine |

The DNA base sequence coding for the various amino acids in this invention is described below.

The bases listed below shall include modified bases such as methylated ones.

| Met | ATG |
|-----|-----|
| Phe | TTT, TTC |
| Ala | GCT, GCC, GCA, GCG |
| Lys | AAA, AAG |
| Arg | AGA, AGG, CGT, CGC, CGA, CGG |
| Thr | ACT, ACC, ACA, ACG |
| Ser | TCT, TCC, TCA, TCG, AGT, AGC |
| Leu | TTA, TTG, CTT, CTC, CTA, CTG |
| Pro | CCT, CCC, CCA, CCG |
| Gly | GGT, GGC, GGA, GGG |
| Tyr | TAT, TAC |
| Val | GTT, GTC, GTA, GTG |
| Glu | GAA, GAG |
| Asn | AAT, AAC |

The various DNA base sequences coding for amino acids listed above can properly be selected for use in this invention.

The DNA consisting of a DNA base sequence or the DNA containing such a sequence coding for the signal amino acid sequence in this invention can be created by means of chemical synthesis or extracted from the chromosomal DNA of certain strains.

The strains used in the method of extracting the DNA from the chromosomal DNA include, for example, *Bacillus subtilis* which has a high α-amylase productivity. The *Bacillus subtilis* of high amylase productivity cited herein includes those strains which have been improved by various means from long ago, such as *Bacillus subtilis* NA 64 strain (IA 412) prepared by incorporating an α-amylase controlling gene of *Bacillus natto* in the *Bacillus subtilis* 6160 strain which has been derived from the *Bacillus subtilis* 168 strain, and it has a peculiar property of secreting plenty of α-amylase out of cells. The NA 64 strain (IA 412) is already widely known and can be obtained easily. For instance, it is readily available from the Bacillus Genetic Stock Center (The Ohio State University). The NA 64 strain (IA 412) has been deposited with the Fermentation Research Institute Agency of Industrial Science and Technology under the deposite number of FERM BP-423.

The preparation of fragments containing a DNA base sequence coding for the signal amino acid sequence in this invention will be embodied by the following example, though this invention shall not be limited to this example.

PREPARATION EXAMPLE

The α-amylase gene was prepared as follows: The chromosomal DNA was prepared from *Bacillus subtilis* NA 64 strain (IA 412) (FERM BP-423) which produces α-amylase, exocellular enzyme, by use of Saito-Miura method (H. Saito et al., Biochem. Biophys. Acta. 72, 619 (1963)).

The temperate phage $\rho 11$ (D. H. Dean et al., J. Virol. 20, 509 (1976)) was prepared as follows: $\rho 11$ particles were obtained by inducing the lysogenic strain of temperate phage $\rho 11$ by treatment with mitomycin C (product of the Kyowa Hakko Kogyo Co., Ltd.).

The $\rho 11$ was purified by the cesium chloride equilibrium density gradient centrifugation method (where the cesium chloride solution prior to the centrifugation was set to a density of 1.51 g/cm$^3$). DNA was prepared from the purified $\rho 11$ particles by the SDS-phenol-ethanol precipitation method.

The chromosomal DNA from *Bacillus subtilis* NA 64 strain and the $\rho 11$ DNA obtained in the abovementioned manner were incised with restriction enzyme BAM HI (a product of the Takara Shuzo Co., Ltd.), and sebsequently linked with T4-ligase (a product of BRL), from which specifically transduced phage particles retaining the α-amylase gene were obtained by use of the method of Kawamura et al. (Gene, 5, 87 (1979)) or the method of Nomura et al. (Agric. Biol. Chem. 43, 2637 (1979)). The resulting specifically transduced phage particles retaining the α-amylase gene were further processed into $\rho 11$ DNA retaining the α-amylase gene by use of the SDS-phenol-ethanol precipitation method.

Subsequently, this $\rho 11$ DNA was partially digested with restriction enzyme Sau 3A (a product of the Takara Shuzo Co., Ltd.). The resultant was linked with the plasmid pUB 110 fragment incised with the restriction enzyme Bam HI by the use of T4 ligase to give a hybrid plasmid mixture.

*Bacillus subtilis* was transformed by the use of this mixture according to the protoplast transformation method (S. Chang and S. N. Cohen, M.G.G., 168, 111 (1979)). Out of the transformed strains were selected such strains that had both resistance to kanamycin (10 μg/ml) and activity of α-amylase. These selected strains were submitted to pure culture in a kanamycin-containing medium (10 μg/ml) and, thereafter, plasmids retained in such cultured cells were prepared by use of the conventional cleared lysate methos. The resulting plasmids were incised with restriction enzyme Eco RI (a product of Boehringer) and Xba I (a product of BRL), and the incised products were submitted to an 0.8% agarose gel electrophoresis and DNA fragment of band centering on about 1.4 Kbp extracted from the gel according to the hydroxyapatite method (H. F. Tabak and R. A. Flavell, Nucleic Acids Research, 5, 2321 (1978)). This fragment was further incised with restriction enzyme Alu I (a product of the Takara Shuzo Co., Ltd.) and the incised product was submitted to a 5% polyacrylamide gel electrophoresis to cut out a fragment at a band of about 0.45 Kbp, so that DNA was extracted with an extraction buffer (0.1M Tris HCl (pH 8.0), 0.5M ammonium acetate and 10 mM EDTA) to give a DNA fragment containing the DNA coding for the signal amino acid sequence as intended in this invention.

The fact that this DNA fragment was coding for the amino acid sequence as intended in this invention was confirmed by analyzing the fragment by use of the Maxam-Gilbert method (Method in Enzymology, vol. 65, 499). The DNA base sequence thus confirmed was as follows:

| ATG | TTT | GCA | AAA | CGA | TTC | AAA |
| ACC | TCT | TTA | CTG | CCG | TTA | TTC |
| GCT | GGA | TTT | TTA | TTG | CTG | TTT |
| TAT | TTG | GTT | CTG | GCA | GGA | CCG |
| GCG | GCT | GCG | AGT | GCT | GAA | ACG |
| GCG | AAC | AAA | TCG | AAT | GAG. | |

APPLICATION EXAMPLE

The DNA fragment obtained in the Preparation Example and the Hind III linker (a product of the Takara Shuzo Co., Ltd.) were linked with T4 ligase by use of the conventional method, incised subsequently with restriction enzyme Hind III (a product of the Takara Shuzo Co., Ltd.), and thereafter submitted to a 5% polyacrylamide gel electrophoresis, so that said fragment linked with the Hind III linker was subsequently extracted from the gel. This DNA fragment will be referred to as A.

On the other hand, pBR 322 was sufficiently incised with the restriction enzyme Eco RI and further incised with exonuclease Bal 31 (a product of BRL) for about 30 seconds, and the resultant was subsequently precipitated with ethanol, so that the DNA was concentrated and purified, and was again incised sufficiently with restriction enzyme Bst N-1 (a product of New England Bio Labs):

The resulting product was subsequently submitted to a 1.2% agarose gel electrophoresis, and thereafter DNA was cut out in the vicinity of 1.4 to 1.5 Kbp and extracted from the gel by use of the hydroxyapatite method. The end portion of the extract was made into double-strand with the *E. coli* DNA polymerase I (Klenow fragment) (a product of BRL) and dNTP (a product of the Yamasa Shoyu Co., Ltd.). The resultant was subsequently linked with the Hind III linker in the same manner as mentioned above, and incised with Hind III. This fragment was then cut out by means of a 1.2% agarose gel electrophoresis, and DNA was extracted. This DNA fragment will be referred to as B.

pUB 110 was incised with the restriction enzyme Bam HI, treated with *E. coli* DNA polymerase I (Klenow fragment) in the same manner, incorporated with Hind III linker, and incised with Hind III, and the resulting product was subsequently submitted to an 0.8% agarose gel electrophoresis in the same manner as mentioned above, so that DNA was extracted. This DNA fragment will be referred to as C.

These three fragments A, B and C were mixed in approximately equal quantities, and the mixture was introduced into the *Bacillus subtilis* protoplast by the conventional method. After regeneration, this was grown in a medium containing 20 µg/ml of ampicillin and 10 µg/ml of kanamycin, whereby a transformation was obtained which was capable of growing on said medium. This *Bacillus subtilis* was submitted to pure culture, and it was immunologically confirmed that an ampicillin-decomposing enzyme was present in the medium.

In the culture of *Bacillus subtilis* in the above Preparation and Application Examples, a modified L-broth (containing 1 g of Bacto tryptone (a product of Difco), 0.5 g of Yeast Extract (a product of Difco), 1.0 g of NaCl and 0.2 g of glucose per 100 ml; pH 7.0) was used in the preparation of p11, while an L-broth (modified L-broth containing 0.5 g of NaCl) was used in other cases.

The buffer solutions used for the enzyme reaction, electrophoresis and DNA extraction herein were all those having known compositions described in relevant manuals, various kinds of literature or guide books.

What is claimed is:

1. Essentially pure DNA consisting essentially of a sequence of DNA bases coding for the signal amino acid sequence:

| Met | Phe | Ala | Lys | Arg | Phe | Lys |
|-----|-----|-----|-----|-----|-----|-----|
| Thr | Ser | Leu | Leu | Pro | Leu | Phe |
| Ala | Gly | Phe | Leu | Leu | Leu | Phe |
| Tyr | Leu | Val | Leu | Ala | Gly | Pro |
| Ala | Ala | Ala | Ser | Ala | Glu | Thr |
| Ala | Asn | Lys | Ser | Asn | Glu. |     |

2. Essentially pure DNA as set forth in claim 1, wherein the sequence of DNA bases coding for the signal amino acid sequence is

| ATG | TTT | GCA | AAA | CGA | TTC | AAA |
|-----|-----|-----|-----|-----|-----|-----|
| ACC | TCT | TTA | CTG | CCG | TTA | TTC |
| GCT | GGA | TTT | TTA | TTG | CTG | TTT |
| TAT | TTG | GTT | CTG | GCA | GGA | CCG |
| GCG | GCT | GCG | AGT | GCT | GAA | ACG |
| GCG | AAC | AAA | TCG | AAT | GAG. |    |

3. A vector containing DNA consisting essentially of the sequence of DNA bases as set forth in claim 1.

4. The essentially pure DNA as set forth in claim 1 consisting of said sequence of DNA bases.

5. The essentially pure DNA as set forth in claim 2 consisting of said sequence of DNA bases.

* * * * *